United States Patent [19]

Takahara et al.

[11] Patent Number: 5,760,265
[45] Date of Patent: Jun. 2, 1998

[54] PROCESS FOR PREPARATION OF AN ESTER UTILIZING AN ESTERIFYING CATALYST

[75] Inventors: Ichiro Takahara; Masumi Kadobayashi; Noriaki Kaminaka, all of Osaka, Japan

[73] Assignee: Matsumoto Yushi Seiyaku Co., Ltd., Osaka, Japan

[21] Appl. No.: 611,162

[22] Filed: Mar. 5, 1996

[30] Foreign Application Priority Data

Mar. 22, 1995 [JP] Japan .................... 7-062516

[51] Int. Cl.$^6$ .................... C07C 67/08; C07C 67/14; C07F 7/28
[52] U.S. Cl. .................... 556/51; 556/52; 560/1; 560/8; 560/99
[58] Field of Search ............ 556/51, 52; 560/1, 560/8, 99

[56] References Cited

U.S. PATENT DOCUMENTS

| | | |
|---|---|---|
| 4,526,725 | 7/1985 | Deardorff . |
| 5,324,853 | 6/1994 | Jones et al. .................... 560/98 |

FOREIGN PATENT DOCUMENTS

| | | |
|---|---|---|
| 52-022592 | 2/1977 | Japan . |
| 53-094296 | 8/1978 | Japan . |
| 56-027504 | 6/1981 | Japan . |
| 61-207358 | 9/1986 | Japan . |
| 62-079849 | 4/1987 | Japan . |
| 62-289236 | 12/1987 | Japan . |
| 2062849 | 3/1990 | Japan . |
| 3294243 | 12/1991 | Japan . |
| 4001156 | 1/1992 | Japan . |
| 5170698 | 7/1993 | Japan . |

Primary Examiner—Johann Richter
Assistant Examiner—Jane C. Oswecki
Attorney, Agent, or Firm—Birch, Stewart, Kolasch & Birch, LLP

[57] ABSTRACT

The present invention provides a process for preparation of an ester comprising reacting a carboxylic acid and an alcohol in the presence of an esterific catalyst comprising at least one compound selected from the group consisting of halides, nitrates, carboxylates, alcoholates and acetylacetone complexes of metals of the titanium group. According to the present process, substantially equal equivalent of the alcohol and the acid can be reacted completely. In addition, the present invention further provides a purification process to eliminate the catalyst from homogeneous reaction system completely.

13 Claims, No Drawings

PROCESS FOR PREPARATION OF AN ESTER UTILIZING AN ESTERIFYING CATALYST

FIELD OF THE INVENTION

The present invention relates to a process for the preparation of an ester. In particular, the present invention provides a process including a step to synthesizing an organic ester by reacting a carboxylic acid and an alcohol under presence of a novel catalyst, and if desired, a step to purify the same in order to eliminate said catalyst.

DESCRIPTION OF THE PRIOR ART

Numerous esters are synthesized from carboxylic acids and alcohols, and are known to be useful in various fields. In addition, esters derived from natural products are used as, for example, oil, fats or flavor.

Formerly, ester synthesizing processes had been developed for the purpose of production of natural esters and played an important role in the development of chemical industry. Recently, such processes have been turned to synthesize novel compounds, and numerous valuable materials have been developed by such processes.

As a way for the preparation of an ester, a lot of protocols are known in the art but the most convenient, cost saving and widely applicable process is dehydration between a carboxylic acid or its anhydride and an alcohol. In the reaction, an acid catalyst, such as sulfate, para-toluene sulfonic acid and a metal oxide, is usually used to cause the reaction to proceed.

A strong acid catalyst, such as sulfonic acid or para-toluene sulfonate, brings various side reactions, for example, dehydration of the alcohol which provides side products such as olefines or ethers, and the reaction between sulfonic acid and the alcohol which provides sulfate ester.

When a relatively weak acid, such as a metal oxide, for example titanium oxide, was used as a catalyst such side reactions could be suppressed but its catalytic activity was not enough. In order to achieve a good yield, an equilibrium of the reaction mixture, i.e., a carboxylic acid and an alcohol, and the product, i.e., an ester, must be shifted toward the product. Thus, an excess quantity of the acid or the alcohol should be reacted with the other and unreacted reactant remained in the product must be eliminated from the product. Since the elimination of such unreacted material is sometimes difficult or impossible, only an ester of low purity could be obtained. Even if such elimination can be effected, there are other problems, for example, the elimination process consumes too much time and energy and may result in a very low yield; and in addition, it is difficult to recycle the recovered unreacted material.

JP. A. 62-289236 describes to use polytitaniumpolyol compositions as an esterification catalyst. However, preparation of the catalyst is difficult. In addition, the reaction mixture is required to contain 25% excess of alcohol than acid. JP. B2, 56-27504 describes titanium and zirconium alkoxydes as esterification catalysts. However, these catalysts are difficult to eliminate from the product because they form colloids during their decomposition step. JP. A, 3-294243 describes clay type adsorptive compositions containing zirconium, however, such a composition is difficult to prepare. JP. A, 53-94296 describes titanium alkoxylate as a catalyst, however, the catalyst is highly expensive and difficult to decompose and eliminate from the product. JP. A, 4-1156 describes hydroxides of IV group metals including zirconium hydroxide as esterification catalysts. However, these catalysts are very difficult to prepare, require a high acid/alcohol ratio, high temperature and long time for reaction, and resulting esters are generally colored.

U.S. Pat. No. 4,526,725 describes a process for preparation of a purified ester in which reacting a carboxylic acid and an excess alcohol in the presence of an alkyltitanium complex as a catalyst, followed by steam distillation of the product to eliminate the unreacted alcohol and convert the titanium residue into undissolved form, and then filtrate the mixture to eliminate the participated catalyst.

SUMMARY OF THE INVENTION

An object of the present invention is to provide a novel process for the preparation of an ester from a substantially equal equivalent of an alcohol and a carboxylic acid, which is substantially free from side products and provides the ester in a good yield.

Accordingly, the present invention provides a process for the preparation of an ester, comprising reacting a carboxylic acid and an alcohol in the presence of an esterific catalyst containing at least one compound selected from the group consisting of halides, nitrates, carboxylates, alcoholates, and acetylacetone complexes of metals of the titanium group.

The esterification activity of the catalyst used in the present invention is higher than that of conventional catalysts including derivatives of metals of the titanium group other than that of the present invention. Therefore, according to the present invention, a substantially equal equivalent of the alcohol to the acid is required for complete esterification of the acid; in addition, the present process provides the ester in a good yield, within a short period of time, under a relatively low temperature.

Since the carboxylate or the acetylacetone complex of a metal of the titanium group, which is one of the above listed catalysts, is dissolved both in the mixture of the starting materials, i.e. the carboxylic acid and the alcohol, and in the product, i.e. the ester, it acts as a homogeneous catalyst in the homogeneous reaction system; and that is the reason why this catalyst shows a superior activity. However, it is sometimes required to eliminate the residual metal of the titanium group from the product. The amount of the metal remained in the resulted ester is little but, in some cases, such a little amount of the metal can exert a bad influence upon use. Since the catalyst is novel for esterification, a method to eliminate the metal from the resulted ester is not known in the art.

Another important object of the present invention is to provide a process for preparing a highly purified ester comprising a purification step to eliminate the catalyst, carboxylate or acetylacetone complex of a metal of the titanium group from the product.

Conventional methods for eliminating metal atoms from a homogeneous system include adding an aqueous solution of a chelating agent into the system. However, since the metal is contained therein as a carboxylate, it cannot be eliminated completely from the system under conventional conditions; and when we, the inventors, added a conventional chelating agent into the resulted ester, the remaining catalyst, metal carboxylate, could not be eliminated completely. Surprisingly, we found that a lowering of the PH value of the aqueous solution of the agent causes the metal to be freed from the carboxylate and to move into aqueous phase.

Accordingly, the present invention further provides a process for the preparation of an ester comprising reacting a carboxylic acid and an alcohol in the presence of at least one carboxylate or acetylacetone complex of a metal of the titanium group and then adding an aqueous solution of a chelating agent into the crude ester to solubilize the metal into the aqueous phase and then remove the aqueous phase from the ester.

According to the present invention, the molar ratio of the chelating agent to the catalyst remained in the reaction system is more than about 3. The amount of the aqueous solution is preferably more than about 5% by weight of the produced ester and the pH value of the solution is preferably less than about 3.

DETAILED DESCRIPTION OF THE PRESENT INVENTION

In the present specification, the term "an ester" means an organic ester. The term "a metal of the titanium group" includes titanium, zirconium and hafnium.

The present invention provides a process for the preparation of an ester comprising reacting a carboxylic acid and an alcohol in the presence of an esterific catalyst containing at least one compound selected from the group consisting of halides, nitrates, carboxylates, alcoholates, and acetylacetone complexes of metals of the titanium group.

Some compounds of the metals of the titanium group have been known in the art as, for example, lewis acid type catalyst for cationic polymerization or alkylation reactions. However, to use such compounds for an esterification reaction was not known. These catalysts used in the present invention show a remarkably high activity over the conventional esterification catalysts.

Examples of the halides of metals of the titanium group used in the present invention include $MX_4$, $MX_3$, $MOX_2$, $MOX_2 \cdot MO_2$, $RMX_3$ and $R_2MX_2$, wherein M represents Ti, Zr or Hf; X may be the same or different and represents a halogen atom; and R represents a hydrocarbon group. Preferably, X is Cl and M is Zr. R may be a saturated or unsaturated hydrocarbon group with or without a side chain, and may have a substituent such as a halogen atom. Preferably, R is an aliphatic, a cycloaliphatic or an aromatic group having 1–40, more preferably, 1–20 carbon atoms.

Most preferable examples of the halides include $ZrCl_4$, $ZrCl_3$, $TiOCl_2$, $Ti(C_2H_5)_2Cl_2$, $ZrOCl_2$, $Zr(C_2H_5)_2Cl_2$ and $Zr(C_6H_5)_2Cl_2$.

A halide of a metal of the titanium group which is commercially available as a lewis acid type catalyst for a cation polymerization or alkylation process, can be used in the present invention as it is.

Examples of the nitrates of metals of the titanium group used in the present invention include $MO(NO_3)_2$, $ROM(NO_3)_3$ $MR(NO_3)_3$ and $MR_2(NO_3)_2$, wherein M represents Ti, Zr or Hf , preferably Ti or Zr, and more preferably, Zr; R represents a hydrocarbon group.

Examples of the carboxylates of metals of the titanium group include $M(R'COO)_4$, $O=M(R'COO)_2$, $R''OM(R'COO)_3$, $(R'O)_2M(R'COO)_2$, $R''M(R'COO)_3$ and $O=M(R'COCHCOO)$, wherein M represents Ti, Zr or Hf; R' and R'' represent hydrogen atoms or hydrocarbon groups independently. Preferably carboxylate is $O=M(R'COO)_2$. Preferably, M is Zr. R' and R'' may be saturated or unsaturated hydrocarbon groups with or without side chains, and may have substituents such as halogen atoms and hydroxy groups. The carboxylate may be induced from a polycarboxylic acid, for example fumaric, malonic, tartaric, phtaric or triimellitic acid. Therefore, $(R'COO)_2$ may represent a dicarboxylic acid residue. Preferably, R' and R'' are aliphatic, cycloaliphatic or aromatic groups having 1–40, more preferably 1–20 carbon atoms. Examples of preferred R' and R'' include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicocyl, docosyl, tricocyl, tetracocyl, pentacocyl, isopropyl, tert-butyl, 2-methylpropyl, 2,2'-dimethylpropyl, 3-methylbutyl, 2-ethylhexyl, vinyl, allyl, 2-butenyl, 6-methyl-4-heptenyl, cyclopentyl, cyclohexyl, methylcyclohexyl, ethylcyclohexyl, cyclohexenyl, 1,3-cyclohexadienyl, phenyl, tolyl, cumethyl, benzyl, benzhydryl, phenethyl, tolythyl and naphthyl groups.

A method for preparing the carboxylate of a metal of the titanium group is as follows:

Into a 1 L four necked flask equipped with a reflux condenser, 1 mole of zirconium oxychloride, 2.1 moles of lauric acid and 2 moles of pyridine are contained. The mixture is stirred for 1 hour at 100° C. under continuous bubbling of nitrogen gas. Then, the salt produced in the reaction mixture is isolated by filtration, and dissolved into petroleum ether. The solution is poured into a separating funnel and washed with aqueous sodium carbonate followed by water. The oil layer is isolated and dried with sodium sulfate. Then, the solvent, petroleum ether, is evaporated under reduced pressure. Consequently, a high viscosity liquid of the objective compound is obtained in 90% yield. The obtained salt is dissolved in mineral terpene to provide a solution for use containing 50 wt % of the salt. Other carboxylate of a metal of the titanium group can be prepared as above.

Examples of alcoholates of metals of the titanium group include $R^2M(OR^3)_3$, $R^2_2M(OR^3)_2$ and $R^2_3M(OR^3)$, wherein M represents Ti, Zr or Hf; $R^2$ and $R^3$ may be the same or different and represent hydrogen atoms or hydrocarbon groups. Preferably, the $R^2$ and $R^3$ are hydrocarbon groups having 1–40, more preferably 1–20 carbon atoms which may have substituent such as halogen atoms and hydroxy groups.

Examples of acetylacetone complexes of metals of the titanium group include $O=M[—OC(R^4)=CHC(=O)R^5]_2$, $(OR)_2M[—OC(R^4)=CHC(=O)R^5]_2$ and $(R'COO)_2M[—OC(R^4)=CHC(=O)R^5]_2$, wherein, M represents Ti, Zr or Hf; R, R', $R^4$ and $R^5$ represent hydrogen atoms or hydrocarbon groups. Preferably, M is Zr; R, R', $R^4$ and $R^5$ are saturated or unsaturated hydrocarbon groups which may have substituent such as halogen atoms or hydroxy groups. More preferably, R, R', $R^4$ and $R^5$ are aliphatic, cycloaliphatic or aromatic groups having 1–40, more preferably, 1–20 carbon atoms. Examples of preferred R' include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicocyl, docosyl, tricocyl, tetracocyl, pentacocyl, isopropyl, tert-butyl, 2-methylpropyl, 2,2'-dimethylpropyl, 3-methylbutyl, 2-ethylhexyl, vinyl, allyl, 2-butenyl, 6-methyl-4-heptenyl, cyclopentyl, cyclohexyl, methylcyclohexyl, ethylcyclohexyl, cyclohexenyl, 1,3-cyclohexadienyl, phenyl, tolyl, cumethyl, benzyl, benzhydryl, phenethyl, tolythyl and naphthyl groups.

A method for preparing the acetylacetone complex of a metal of the titanium group is as follows:

Sodium hydroxide and acetylacetone are mixed into water and the mixture is stirred, then sodium acetylacetone becomes to be precipitates; the participate is isolated and dried. Two moles of the obtained sodium acetylacetone and 1 mole of $TiOCl_2$ are mixed with toluene and the mixture is stirred at 100° C., then titanium acetylacetonate and NaCl are produced. NaCl is removed from the mixture by filtration and the filtrate is evaporated, thus, the titanium acetylacetone complex is obtained.

In the present invention, the synthesizing step of an ester in the presence of the catalyst specific to the present invention can be practiced by reacting an alcohol and a carboxylic acid in a conventional fashion. For example, when the catalyst is solid type catalyst such as halides or nitrates, solid powder of the catalyst can be dispersed into the mixture of the alcohol and the acid. When the catalyst is a liquid type one, it can be dissolved into the reaction system and the reaction can be proceed as homogenized system.

The carboxylic acid reacted with the alcohol according to the present invention may be an aliphatic monocarboxylic acid such as caproic acid, caprylic acid, capric acid, lauric acid, myristic acid, oleic acid and stearic acid; an aliphatic dicarboxylic acid such as maleic anhydride, maleic acid, fumaric acid, adipic acid, sebacic acid and azelaic acid; and an aromatic polycarboxylic acid such as phthalic acid, phthalic anhydride, isophtalic acid, trimellitic acid, pyromellitic acid and pyromellitic anhydride; or polymerized carboxylic acid such as polyacrylic acid.

The alcohol reacted with the carboxylic acid according to the present invention may be aliphatic primary alcohols, such as butanol, hexanol, heptanol, octanol, 2-ethylhexanol, decanol, dodecanol and stearyl alcohol; aromatic primary alcohols, such as benzyl alcohol; or polyhydric alcohols, such as ethylene glycol, propylene glycol, neopentyl glycol, trimethylol propane, trimethylol ethane, pentaerythritol, dipentaerythritol, sorbitol and polyvinyl alcohol.

According to the present invention, a chemical equivalent of the alcohol to the carboxylic acid may be about 1.0–1.1. This is a great advantage of the present invention in that a substantially equal equivalent of the alcohol and the carboxylic acid can react almost completely to provide the ester in almost 100% yield within a relatively short period of time.

The amount of the catalyst based on the weight of the metal of the titanium group is between 1 ppm and 5000 ppm, preferably between 10 ppm and 1000 ppm by total weight of the carboxylic acid and the alcohol.

The reaction temperature is between 50° and 300° C., preferably 120° and 240° C. In case of the carboxylic acid being a polycarboxylic acid such as di- or tricarboxylic acid, more than 200° C. is preferable.

Since the esterification process is a reversible one, to remove the produced water from the reaction mixture during the reaction is essential for the process to proceed. The removal of the water can be effected by means of reduced pressure or of a co-boiling agent such as xylene. In addition, the water can be eliminated only by bubbling the reaction system with nitrogen gas which is usually introduced into the reaction system to prevent coloring of the resulted ester.

The reaction can be monitored by acid and hydroxy values of the system. In case of a solid type catalyst, after completion of the reaction, the catalyst can be eliminated from the crude product only by filtration or centrifugation of the reaction mixture.

In case of a homogeneous system, the remaining catalyst is dissolved in the resultant ester. To eliminate the catalyst, a solid absorbent agent, on to which the catalyst is absorbed, can be added into the crude product and then the catalyst can be eliminated together with the agent by filtration or centrifugation of the mixture.

Examples of the absorbent agents include active carbonate, synthetic zeolite, natural zeolite, silica-gel, activated clay, activated alumina, charcoal bone, carbon, bauxite, magnesia and flas-earth, and preferably activated carbonate.

In addition to the purification with the assistance of the absorbent agent as above, the carboxylate or acetylacetone complex catalyst can be eliminated as a water soluble metal complex from the product. According to this purification step, an aqueous solution of a chelating agent is added into the crude product, and the agent attaches to the metal to form a water soluble metal complex, then the aqueous phase containing the metal can be separated from the ester phase.

The preferable chelating agents are carboxyl acid type agents which able to keep the pH value of their aqueous solution below about 3. Examples of the agents include ethylenediamine tetraacetic acid (EDTA 4H), hydroxy ethylimino diacetic acid, nitlirotriacetic acid, diethylenetriamine penta acetic acid and triethylene tetramine hexaacetic acid and mixtures thereof. However, even if the chelating agents which can keep the pH values of their aqueous solutions below 3, amine trimethylene phosphoric acid, 1-hydroxyethylidene-1,1'-diphosphoric acid and ethylenediamine tetra(methylenephosphoric) acid are not preferable for the present invention, since they cause slightly saponification or coloration of the ester or they are partially dissolved into the ester.

By means of these carboxylic acid type chelating agents, the metal atoms in the crude product become free from the carboxyl groups and the agent attaches to the metal atoms to form the complex which is able to be dissolved into the aqueous phase. Consequently, by separating the aqueous phase from the reaction system, the metal can be completely eliminated from the ester product. The ester purified according to the present step is free from saponification or coloration which is a disadvantage of an ester purified with a mineral acid.

According to the present invention, the molar ratio of the chelating agent to the residual metal catalyst existing in the crude ester is preferably more than about 3, more preferably about 3–5. If the ratio were more than 5, only the same result could be obtained, so, it would not economical.

According to the present invention, the amount of the aqueous solution may be more than 5%, preferably 5–30% by weight of the ester. If the amount is less than 5 wt %, metals in the crude product cannot be eliminated completely, whereas, if it is more than 30 wt %, metal removing ability does not change and the amount of waste water becomes too much.

The purification step of the present invention consisting of the following steps:

a) Mix the aqueous solution of the chelating agent into the crude product containing the residual catalyst, carboxylate or acetylacetone complex of a metal of the titanium group;

b) Heat the system to form a metal complex of the agent;

c) Allow the system to stand to allow the aqueous phase to separate from the ester phase;

d) Remove the aqueous phase;

e) Heat the ester phase to eliminate the water remaining in the ester;

f) Filtrate the ester to the chelating agent and metal complex remains in the product.

The reaction for forming the metal complex may be practiced under atmospheric pressure, at 70°–100° C. for 5 minutes-1 hour. Depending on the required purity, the steps a)–f) can be repeated.

The invention will be understood more readily with reference to the following examples; however these examples are intended to illustrate the invention and are not to be construed to limit the scope of the invention.

EXAMPLE 1

Into a 1 L four necked separable flask, 1 mole of capric acid and 1.03 moles of stearyl alcohol were contained, then titanium tetrachloride (ISHIZU SEIYAKU Co., Ltd., 1st grade) was added into the mixture to give the titanium tetrachloride concentration of 2000 ppm by total weight of the carboxylic acid and the alcohol. The titanium tetrachloride should be treated in dried box to evade humidity, and the reaction should be practiced in a draft chamber because hydrochloride gas is produced during the reaction. A propeller type stirrer, a reflux condenser, a mercury thermometer and a nitrogen inducing tube were equipped on the separable flask. The separable flask was kept on an oil bath and nitrogen gas was bubbled into the stirred mixture. The mixture was reacted at 190° C. for 3 hours. With the progress of the reaction, formed water was removed through the separator equipped on the reflux condenser. After three hours reaction, the acid value of the reaction mixture was 0.5. The separable flask was allowed to cool to room temperature, with continuous stirring and bubbling. Then, the contents in the separable flask were filtrated through a glass filter to remove the solid type catalyst. The filtrate was poured into a separating funnel and washed with diluted sodium carbonate, followed by deionized water. After elimination of the residual water, final yield of the product was 98%. IR and NMR analysis showed that the product contained 99 wt % of stearyl caprylate and 1 wt % of stearic alcohol. Hue was determined to be G(Gardnar) 1.

EXAMPLE 2

In a 1 L four necked flask, one mole of maleic anhydrous and 2.05 moles of lauryl alcohol were contained, and zirconium oxychloride was added into the mixture to give a zirconium oxychloride concentration of 1000 ppm by total weight of the acid and the alcohol. The mixture was reacted as the example 1 above at 200° C. for 4 hours. After 4 hours, the acid value of the mixture was, 0.3. The product was purified according to the example 1 to obtain the ester as a colorless product. The yield was 99%.

EXAMPLE 3

In a 2 L four necked flask, 1 mole of sebacic acid and 2.2 moles of octanol were contained, and zirconium naphtenate, which was previously prepared in the above described manner, was added into the mixture to give a zirconium naphtenate concentration of 1000 ppm by total weight of sebacic acid and octanol. The mixture was reacted as the example 1 at 190° C. After three hours, the acid value of the mixture was 0.5, and at the time, that reflux was stopped. The residual alcohol was eliminated by heating the mixture under reduced pressure. The yield of the product per sebacic acid was almost 100%. Fifty grams of an active carbon absorbent agent was added into the crude product and stirred the dispersion mixture for 3 hours to absorb the zirconium naphtenate on the agent completely. Then, the absorbent agent was removed from the product by filtration. The resulted octylsebacate ester had a 99% purity and was substantially colorless.

EXAMPLE 4

Zirconium acetate was previously prepared in the above described manner from zirconium oxychloride and acetic acid. Into an 1 L four necked flask, 1 mole of 1-naphthoic acid and 1.02 moles of myristyl alcohol were contained, and the zirconium acetate was added into the mixture to give the zirconium acetate concentration of 5000 ppm by total weight of the acid and the alcohol. The mixture was reacted as the example 1 at 190° C. After five hours, the acid value of the mixture was 0.7 and the reaction was stopped at that time. The hydroxy value of the product was 2.1.

EXAMPLE 5

Into an 1 L four necked flask, 1 mole of linoleic acid and 1.02 moles of cetyl alcohol were contained, and acetylaceto titanate was added into the mixture to give the acetylaceto titanate concentration of 5000 ppm by total weight of the acid and the alcohol. The mixture was reacted as the example 1 at 190° C. for 3 hours. The acid value of the product was 0.2. The product was colorless.

EXAMPLE 6

Into an 1 L four necked flask, 1 mole of myristic acid and 1.3 moles of decanol were contained, and zirconium nitrate was added into the mixture to give the zirconium nitrate concentration of 1000 ppm by total weight of the acid and the alcohol. The mixture was reacted as the example 1 at 190° C. for 3 hours. The acid value of the product was 0.5. Thirty grams of active carbon absorbent agent was added into the crude product and the dispersion mixture stirred at 130° C. for 1 hours to absorb the zirconium completely. Then, the absorbent agent was removed from the product by filtration. The resulted product contained less than 1 ppm of zirconium. The acid value of the product was 0.3 and the hydroxy value was 2.1.

EXAMPLES 7–15

In the examples 7–15, various combination of carboxylic acids and alcohols were reacted in the presence of various catalyst. The amount of the respective reactant and the catalyst, reaction temperature and reaction time are shown in the table 1. Conditions other than those shown in the table 1 were the same as the example 1. The acid and hydroxy values of the obtained esters are shown in the table 2.

TABLE 1

| example No. | carboxylic acid | alcohol | molar ratio *1 | catalyst | amount *2 | temp. (°C.) | time (Hr) |
|---|---|---|---|---|---|---|---|
| 7 | caproic acid | pentaerythritol | 0.258 | $ZrO(CH_3COO)_2$ | 500 | 190 | 5 |
| 8 | capric acid | glycerine | 0.343 | $ZrO(C_7H_{15}COO)_2$ | 200 | 190 | 5 |
| 9 | 2-ethylhexanoic acid | oleyl alcohol | 1.02 | $ZrO(C_{17}H_{35}COO)_2$ | 300 | 190 | 3 |
| 10 | myristic acid | 2-ethylhexanol | 1.05 | $Ti(OC_4H_9)_2(C_4H_7COO)_2$ | 100 | 190 | 3 |
| 11 | palmitic acid | lauryl alcohol | 1.02 | $Zr(C_4H_7COO)_4$ | 500 | 190 | 3 |
| 12 | telephtalic acid | myristyl alcohol | 2.04 | $ZrO(C_6H_5COO)_2$ | 800 | 190 | 3 |

TABLE 1-continued

| example No. | carboxylic acid | alcohol | molar ratio *1 | catalyst | amount *2 | temp. (°C.) | time (Hr) |
|---|---|---|---|---|---|---|---|
| 13 | telephtalic anhydride | amyl alcohol | 2.04 | TiO(=CHCOO)$_2$ | 300 | 190 | 4 |
| 14 | adipic acid | trimethylol propane | 0.7 | TiO(C$_{17}$H$_{33}$COO)$_2$ | 200 | 190 | 5 |
| 15 | oleic acid | glycerin | 0.343 | ZrO(C$_{17}$H$_{32}$(OH)COO)$_2$ | 200 | 190 | 5 |

*1: molar ratio of the alcohol to carboxylic acid
*2: amount of the metal contained in the catalyst by the total weight of the carboxylic acid and the alcohol (ppm)

TABLE 2

| | product | | |
|---|---|---|---|
| example No. | acid value | hydroxy value | residual metal (ppm) |
| 7 | 0.5 | 2.1 | 1.1 |
| 8 | 0.7 | 1.8 | 0.3 |
| 9 | 0.3 | 1.5 | 1.5 |
| 10 | 0.8 | 3.0 | 0.2 |
| 11 | 0.3 | 2.2 | 0.05 |
| 12 | 0.2 | 1.6 | 0.1 |
| 13 | 0.9 | 2.9 | 0.3 |
| 14 | 0.4 | 2.1 | 2.1 |
| 15 | 0.3 | 2.2 | 1.1 |

COMPARATIVE EXAMPLE 1

Into an 1 L-four-necked flask, 1 mole of oleic acid and 1.1 moles of stearic acid were contained, and a catalyst para-toluene sulfonate was added into the mixture to give the para-toluene sulfonate concentration of 0.5% by total weight of the acid and the alcohol. The mixture was reacted as in the example 1, at 220° C. After 20 hours, the acid value of the mixture was 2.5. Forty hours of reaction were required to decrease the acid value lower than 1.0. The resulted ester was dark blown because of a side reaction owing to the catalyst.

COMPARATIVE EXAMPLE 2

The comparative example 1 was repeated except for adding no catalyst. After 40 hours reaction, the acid value of the reaction mixture was still 2.0. After an additional 10 hours reaction, the acid value did not change and the reaction was stopped. The resulted ester was brown because it heated too long time.

COMPARATIVE EXAMPLE 3

Myristyl 1-naphthoate was synthesized according to the example 4 except for cobalt naphtenate was used as a catalyst instead of zirconium. After 5 hours reaction, the acid value of the reaction mixture was 3.8. An additional 5 hours reaction lowered the acid value only to 3.4.

EXAMPLE 16

Three hundreds grams of the crude ester obtained from example 3 (containing 0.0016 molar zirconium) was contained into a 50 ml four necked flask, and 30 g of ion-exchanged water and 1.5 g (0.005 mole) of EDTA 4H were added into the flask. The mixture was vigorously stirred at 80° C. for 30 minutes under continuous bubbling of nitrogen gas. After completion of the reaction, the flask stood under the same temperature for 2–3 hours to allow the aqueous phase separate from the ester phase. Then, the aqueous phase was removed and the ester phase was heated to 120°–145° C. under normal pressure, with continuous bubbling of more than 2 L/hr of nitrogen gas to remove the residual water from the ester. As the water was removed, the chilating agent and the metal complex dissolved in the water were precipitated, then, the precipitates were filtered off. The filtrate was colorless.

The resulted ester contained 0.1 ppm of zirconium and had an acid value of 0.1 and hydroxy value of 1.1.

EXAMPLES 17–22

The example 16 was repeated except for the conditions of table 3 below. The results are also shown in the table 3.

TABLE 3

| No. | ester | catalyst | chelating agent | amount *1 | time (Hr) | temp. (°C.) | result *2 |
|---|---|---|---|---|---|---|---|
| 17 | stearyl-caprylate | zirconium naphtenate | EDTA | 3 | 0.5 | 80 | 0.05 |
| 18 | lauryl-myristate | zirconium acetate | nitrilo triacetic acid | 4 | 1 | 90 | 0.1 |
| 19 | nonyl-myristate | zirconium octanate | triethylene tetramine hexa aceticacid | 4 | 0.2 | 90 | 0.1 |
| 20 | isoamyl-myristate | titanium acetate | diethylene triamine penta aceticacid | 3 | 0.5 | 80 | 0.1 |
| 21 | olein | zirconium naphtenate | nitrilotri aceticacid | 3 | 0.2 | 85 | 0.2 |
| 22 | tri-methylol propane adipate | zirconium acetate | EDTA | 4 | 0.5 | 90 | 0.1 |

*1: molar ratio of the chilating agent to the catalyst
*2: amount of residual catalyst by the weight of the ester (ppm)

What is claimed is:

1. A process for the preparation of an ester, comprising the step of:

reacting a carboxylic acid and an alcohol in the presence of an esterifying catalyst that comprises at least one compound selected from the group consisting of carboxylates of metals of the titanium group having the formula O=M(R'COO)$_2$, wherein M represents Ti, Zr or Hf, and R' represents a hydrogen atom or hydrocarbon group.

2. A process for the preparation of an ester, comprising the step of:

reacting a carboxylic acid and an alcohol in the presence of an esterifying catalyst that comprises at least one compound selected from the group consisting of halides, nitrates, carboxylates, alcoholates and acetylacetone complexes of metals of the titanium group; and wherein a chemical equivalent of the alcohol to the carboxylic acid is between about 1.0 and 1.1.

3. A process according to claim 2, wherein said at least one compound is a carboxylate of a metal of the titanium group that is selected from the group consisting of $M(R'COO)_4$, $O=M(R'COO)_2$, $R''OM(R'COO)_3$, $(R''O)_2M(R'COO)_2$, $R''M(R'COO)_3$ and $O=M(R'COCHCOO)$, wherein M represents Ti, Zr or Hf, and R' and R'' may be the same or different and represent hydrogen atoms or hydrocarbon groups.

4. A process for the preparation of an ester, comprising the steps of:

reacting a carboxylic acid and an alcohol in the presence of an esterifying catalyst that comprises at least one compound selected from the group consisting of halides, nitrates, carboxylates, alcoholates and acetylacetone complexes of metals of the titanium group to give an ester, and purifying the resulting ester by (i) adding an aqueous solution of a chelating agent into the crude ester to solubilize the metal into the aqueous phase and (ii) separating the aqueous solution from the ester.

5. A process according to claim 1, 2 or 4, wherein said metal of the titanium group is Ti or Zr.

6. A process according to claim 1, 2 or 4, wherein the amount of the esterifying catalyst used is between about 1–5000 ppm by total weight of the carboxylic acid and the alcohol.

7. A process according to claim 4, wherein the amount of said aqueous solution is more than about 5% by weight of the crude ester and the molar ratio of the chelating agent to the residual metal is more than about 3.

8. A process according to claim 4, wherein pH value of said aqueous solution of the chelating agent is less than about 3.

9. A process according to claim 4, wherein said chelating agent is selected from the group consisting of ethylene diamine tetra acetic acid, hydroxyethylimino diacetic acid, nitrilotriacetic acid, diethylenetriamine penta acetic acid and triethylene tetramine hexa acetic acid, and mixtures thereof.

10. A process according to claim 1, 2 or 4, wherein the amount of the esterifying catalyst used is between 10–10,000 ppm by total weight of the carboxylic acid and the alcohol.

11. A process according to claim 9, wherein said cheating agent is selected from the group consisting of ethylene diamine tetra acetic acid, hydroxyethylimino diacetic acid, nitrilotriacetic acid, diethylenetriamine penta acetic acid and triethylene tetramine hexa acetic acid, and mixtures thereof.

12. A process according to claim 8, wherein said cheating agent is selected from the group consisting of ethylene diamine tetra acetic acid, hydroxyethylimino diacetic acid, nitrilotriacetic acid, diethylenetriamine penta acetic acid and triethylene tetramine hexa acetic acid, and mixtures thereof.

13. A process according to claim 4, wherein said at least one compound is a carboxylate or an acetylacetone complex of a metal of the titanium group.

* * * * *